(12) United States Patent
Hively

(10) Patent No.: US 8,740,988 B1
(45) Date of Patent: Jun. 3, 2014

(54) BARIATRIC BALLOON APPARATUS

(76) Inventor: Robert L. Hively, Dunbar, WV (US)

( * ) Notice: Subject to any disclaimer, the term of this patent is extended or adjusted under 35 U.S.C. 154(b) by 0 days.

(21) Appl. No.: 13/544,611

(22) Filed: Jul. 9, 2012

Related U.S. Application Data

(63) Continuation-in-part of application No. 11/155,400, filed on Jun. 16, 2005, now Pat. No. 8,216,266.

(51) Int. Cl.
*A61M 29/00* (2006.01)
(52) U.S. Cl.
USPC ............ 623/23.65; 623/23.67; 606/192
(58) Field of Classification Search
USPC ............ 606/153, 191–195; 623/23.64–23.65, 623/23.67–23.68; 604/99.01–99.04, 96.01, 604/101.05, 908; 128/898
See application file for complete search history.

(56) References Cited

U.S. PATENT DOCUMENTS

| | | | | |
|---|---|---|---|---|
| 3,570,494 | A * | 3/1971 | Gottschalk | 606/196 |
| 4,694,827 | A * | 9/1987 | Weiner et al. | 606/192 |
| 5,634,883 | A * | 6/1997 | Chin et al. | 600/204 |
| 7,244,270 | B2 * | 7/2007 | Lesh | 623/1.11 |
| 7,261,720 | B2 * | 8/2007 | Stevens et al. | 606/105 |
| 7,479,161 | B1 * | 1/2009 | Wassermann et al. | 623/23.65 |
| 7,744,652 | B2 * | 6/2010 | Morsi | 623/23.72 |
| 8,075,582 | B2 * | 12/2011 | Lointier et al. | 606/192 |
| 2002/0055757 | A1 * | 5/2002 | Torre et al. | 606/192 |
| 2003/0194520 | A1 * | 10/2003 | Simhambhatla | 428/35.7 |
| 2003/0236544 | A1 * | 12/2003 | Lunsford et al. | 606/190 |
| 2005/0267595 | A1 * | 12/2005 | Chen et al. | 623/23.65 |
| 2006/0058829 | A1 * | 3/2006 | Sampson et al. | 606/192 |

\* cited by examiner

*Primary Examiner* — Mark Mashack
(74) *Attorney, Agent, or Firm* — Patent Law & Venture Group; Gene Scott

(57) ABSTRACT

A bariatric balloon having a gas-filled antral chamber of a flexible sheet material, the antral chamber having an elastic superior wall joined peripherally with a less-elastic annular wall, the annular wall further joined peripherally with a non-elastic inferior wall, the inferior wall of a more rigid character than the superior wall and the annular wall. The superior wall has a convex shape, the annular wall has a cylindrical shape, and the inferior wall has a planar shape. Secured below the antral chamber, a gas filled pyloric chamber joined to, and contiguous with, the antral chamber, a pyloric wall encompasses the cyloric chamber. The gas-filled antral and pyloric chambers define a volume less than the volume of a human stomach. Safety arms are mounted on a gas inlet/outlet valve and extend radially from the valve in order to prevent the deflated balloon from passing through the pyloric sphincter.

5 Claims, 4 Drawing Sheets

BARIATRIC BALLOON APPARATUS

RELATED APPLICATIONS

This application is a continuation-in-part application of non-provisional parent patent application Ser. No. 11/155,400, filed on Jun. 16, 2005, issued as U.S. Pat. No. 8,216,266 on Jul. 10, 2012, and claims international date priority therefrom. The subject matter of application Ser. No. 11/155,400 is hereby incorporated hereinto in its entirety.

BACKGROUND

No federally sponsored research or development, and no sequence listing, table, or computer program listing compact disc appendix is applicable to this application.

This disclosure relates to the field of medical approaches to human weight loss and body weight maintenance, and more particularly to the use of the bariatric balloon.

Overweight and obesity are rising medical problems of pandemic proportions in the United States, Western Europe and elsewhere, and produce many detrimental health effects. Individuals with a BMI (Body Mass Index) exceeding a healthy number, generally considered to be 30 kg/m$^2$ have a much greater risk of medical issues including: heart disease, diabetes, many types of cancer, asthma, obstructive sleep apnea, and chronic musculoskeletal problems. There is also an effect of obesity on mortality. The obese typically find it difficult to lose weight on their own. It is common for dieters who have tried fad diets to find that they actually gain weight, or return to their original weight after ceasing the diet. First-line treatments for controlling body weight such as diet, exercise, behavior therapy and anti-obesity drugs, in the case of severe obesity, have had limited short-term success and very poor long-term success.

Weight loss surgery generally results in significant weight loss which may lead to improvements in quality of life and the avoidance of obesity related diseases. Bariatrics is the branch of medicine that deals with the causes, prevention, and treatment of obesity. Bariatric surgery is a successful approach to weight loss; examples including gastroplasty surgery, gastric bypass surgery, and jejunoileal bypass surgery. Surgeries for reducing the size of the stomach can cause significant weight loss by reducing the production of ghrelin, the hormone that causes hunger. A smaller stomach demands a change in diet reducing daily caloric intake. A gastric band is a commonly used device in bariatric treatment. The band is placed around the stomach through surgery and constricts the stomach completely until a new, smaller stomach pouch is formed. The band can be adjusted post-surgery by injecting saline into a corded transmitter connected to the band. Creating the restriction allows the patient to eat the right amount of food for loss of weight and maintenance of body weight thereafter. However, if one fails to eat the right foods, he/she may not receive the nutrients required for proper health. Surgical solutions, of course, have many well-known problems including: potential for infection, production of detrimental body adhesions, changes in skin surface contour, foreign body rejection effects, relatively high cost, and so on. A simpler and more cost effective approach is the well-known bariatric balloon such as defined in my earlier referenced application.

The prior art teaches the construction, placement, use, and removal of bariatric balloons. However, a major problem with the actual use of the bariatric balloon is that when food has entered the stomach it lies on top of the bariatric balloon and when a glass of water or other beverage is then ingested, the liquid is able to flush this food around the balloon thereby clearing the antral pouch allowing the patent to continue eating. The present disclosure distinguishes over the prior art and extends this technology by teaching a bariatric balloon with a novel safety device for preventing a deflated balloon from passing through the pyloric sphincter, and a means for preventing the flushing of food out of the fundal pouch in order to eliminate a "full" feeling which leads to over-eating, and, of course, tends to negate the balloon's function.

SUMMARY

A bariatric balloon made of a flexible material has an antral chamber having an elastic superior wall joined peripherally with a less-elastic annular wall, the annular wall further is joined peripherally with a non-elastic inferior wall, the inferior wall having a more rigid character than the superior wall and the annular wall. The superior wall has a convex shape, the annular wall has a cylindrical shape, and the inferior wall has a planar shape. Secured below the antral chamber, an gas filled pyloric chamber is joined to, and contiguous with, the antral chamber. The gas-filled antral and pyloric chambers define a volume less than the volume of a human stomach. Safety arms are mounted on a medially positioned gas inlet/outlet valve and extend radially from the valve in order to prevent a deflated balloon from passing through the pyloric sphincter.

One objective of the present device is to enable the separate inflation and deflation of plural independent balloon chambers.

A further objective is to prevent the balloon from passing through the pylorus in case of sudden deflation.

A still further objective is to adjust the stomach volume occupied by the balloon without removing the balloon from the stomach.

A still further objective, and critical benefit, is to prevent the flushing of ingested food past the balloon before it is digested.

Other features and advantages of the described apparatus and its method of use will become apparent from the following more detailed description, taken in conjunction with the accompanying drawings, which illustrate, by way of example, the principles of the presently described apparatus and method.

BRIEF DESCRIPTION OF THE DRAWINGS

The accompanying drawings illustrate at least one of the best mode embodiments of the present apparatus and method of it use. In such drawings.

DETAILED DESCRIPTION

The above referenced drawing figures illustrate the described apparatus and its method of use in at least one of its preferred, best mode embodiment, which is further defined in detail in the following description. Those having ordinary skill in the art may be able to make alterations and modifications to what is described herein without departing from its spirit and scope. Therefore, it is to be understood that what is illustrated is set forth only for the purposes of example and that it should not be taken as a limitation in the scope of the present apparatus and method of use.

Figure 1:
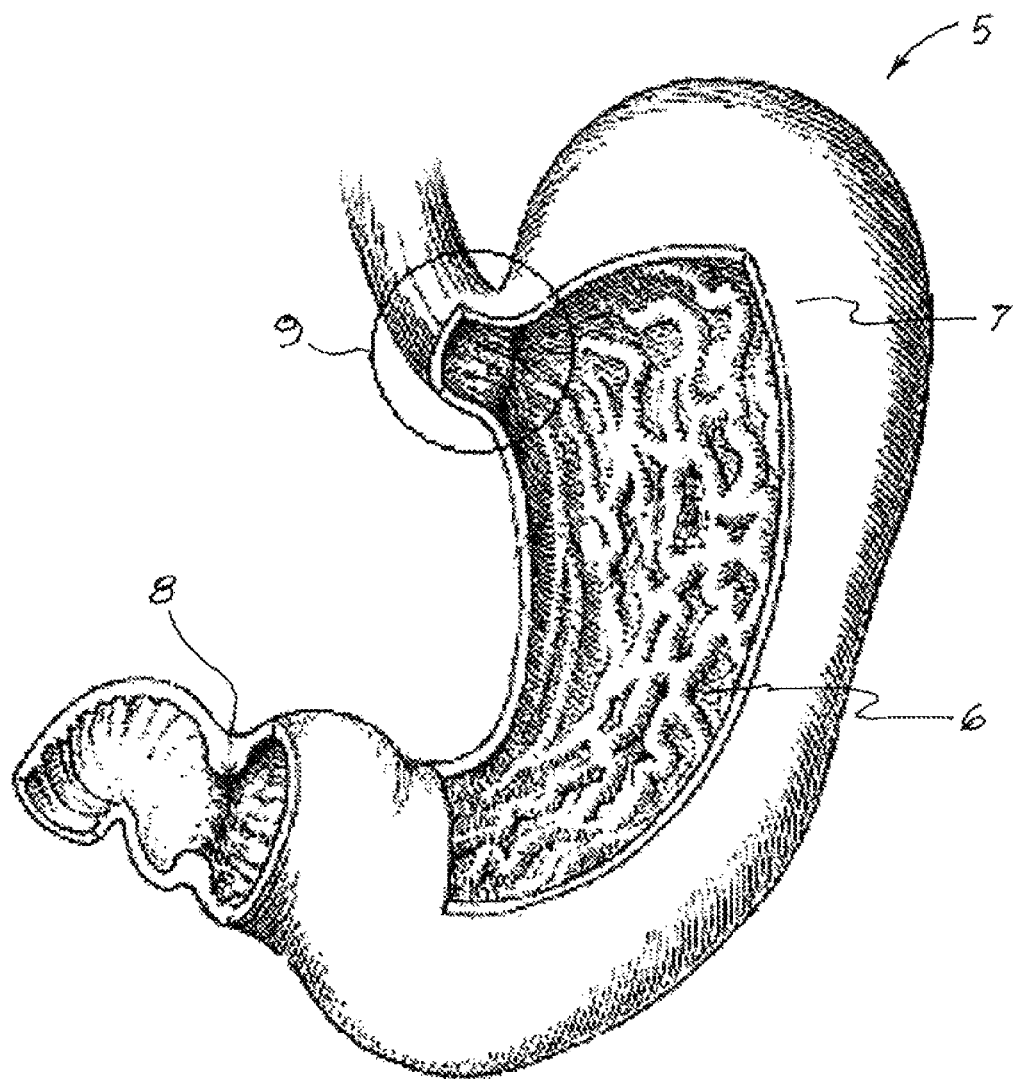
FIG. 1 is an example side elevational view of the human stomach with partial cutaway of a wall thereof to show interior details.
Figure 2:
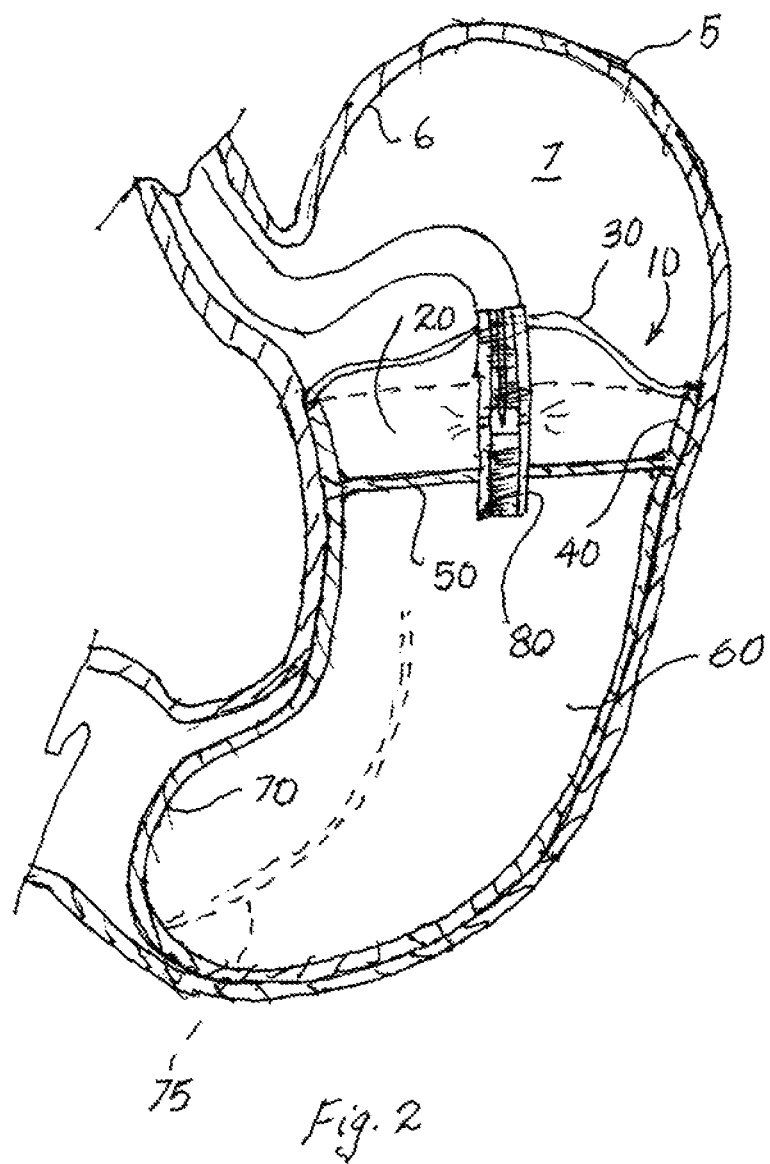
FIG. 2 is an example sectional view thereof with the presently described apparatus inserted therein and showing a means for inflating said apparatus.
Figure 3:
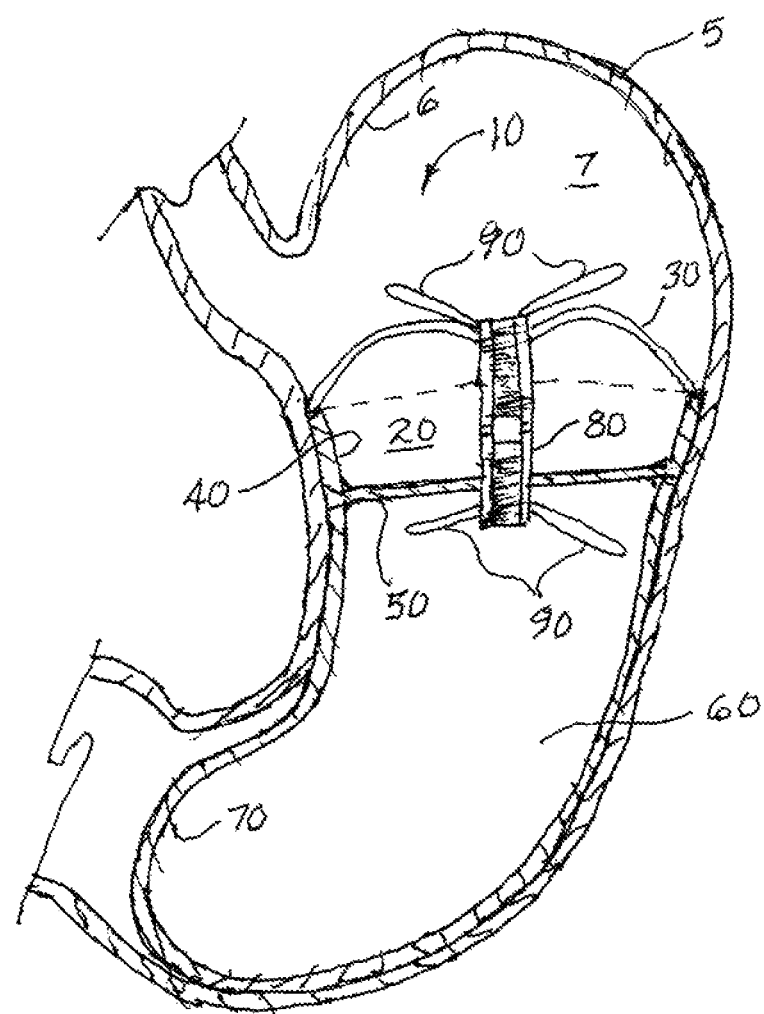
FIG. 3 is a further example sectional view as in FIG. 2 now showing the presently described apparatus as fully inflated.
Figure 4:
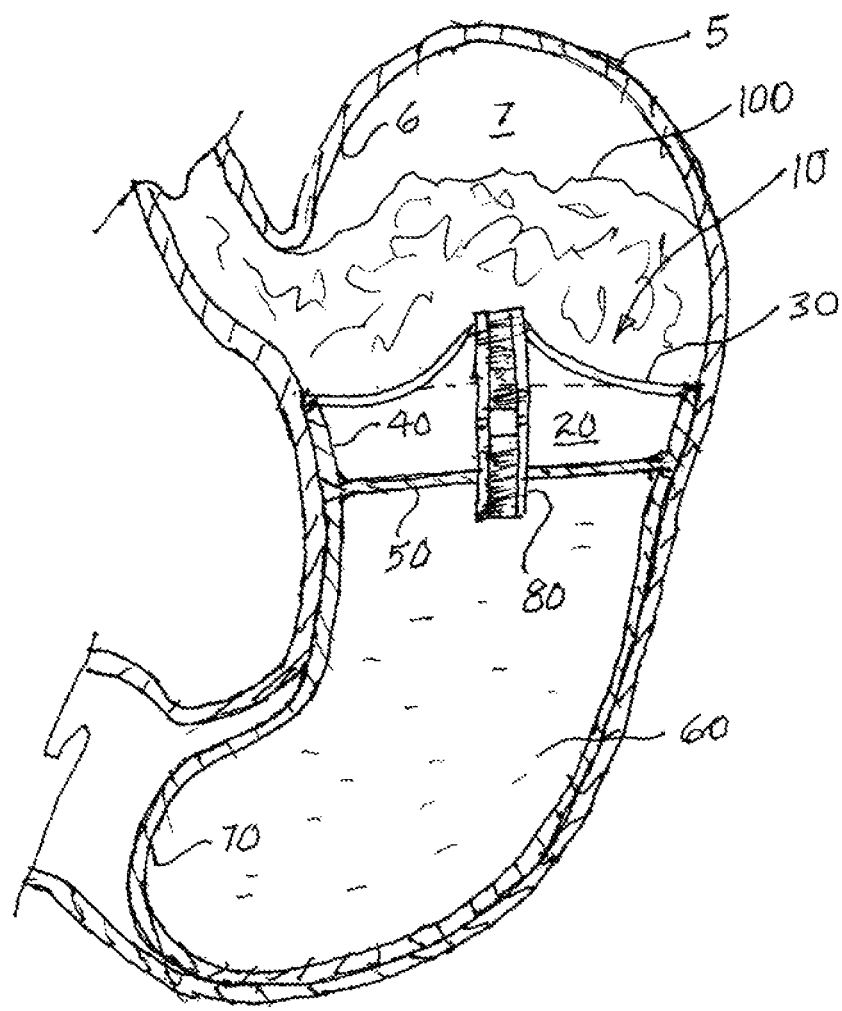
FIG. 4 is a still further example sectional view as in FIG. 2 now showing the presently described apparatus as fully inflated with ingested food lying atop.

As shown in FIGS. 2-4, the presently described and claimed apparatus is a bariatric balloon 10 for placement into a human stomach 5, see FIG. 1, the apparatus having a gas-filled antral chamber 20 of a flexible sheet material such as latex rubber, the antral chamber 20 having an elastic superior wall 30 joined peripherally with a less-elastic annular wall 40, the annular wall 40 further joined peripherally with a non-elastic inferior wall 50, the inferior wall 50 of a more rigid character than the superior wall 30 and the annular wall 40, the superior wall 30 having a convex shape when the balloon 10 is fully filled with a gas by a means shown in FIG. 2, and the stomach 5. The annular wall 40 has a cylindrical shape, and the inferior wall 50 has a planar shape as shown.

Secured below the antral chamber 20 is a gas filled pyloric chamber 60 joined to, and contiguous with, the antral chamber 20 is a pyloric wall 70 encompassing the pyloric chamber 60.

Together, the gas-filled antral 20 and pyloric 60 chambers define a volume, as shown, that is less than the volume of a human stomach 5 leaving an open volume referred to as the antral pouch which is the volume within the stomach 5 where digestion processes occur when the apparatus is in place. The remainder of the stomach volume is filled by the apparatus and cannot participate with digestion.

The bariatric balloon 10 further has a tubular valve 80 medially joined with the antral 20 and pyloric 60 chambers, the tubular valve 80 having a means for exchanging gas with the two chambers in order to fill the stomach cavity but leaving an antral pouch 7 in the stomach's fundus, above the antral chamber 20.

At least one of the superior wall 30, the annular wall 40, and the pyloric wall 70 has an external open channel 75 thereon (FIG. 2) and may have plural such channels 75 in order to allow digested matter to move from the antral pouch 7 to the pyloric sphincter 8 shown in FIG. 1. Such channels 75 may be about 2 to 4 mm wide which allows them to pass digested matter while either preventing or slowing movement of non-digested materials.

Two or more safety arms 90 may be secured to and extended radially outwardly from the tubular valve 80 and may be attached thereto at its upper end adjacent to the superior wall 30, or may be attached within balloon 10 near the lower end of valve 80. Should balloon 10 deflate within the stomach 5 it might be possible for it to pass through the pyloric sphincter 8 and into the small bowl where retrieval will require surgery. The arms 90 will prevent this occurrence as their length and full circumference is greater then the opening of the sphincter 8. See FIG. 3.

The novelty of the present apparatus is in its ability to prevent the balloon 10 from being swallowed into the small bowel. Further novelty is in the operating characteristics of the anteral chamber 20. It is shown in FIG. 3 that when the chamber 20 is fully inflated, the elastic superior wall 30 being more elastic then the annular wall 40 and the inferior wall 50, assumes an expanded convex shape as shown in FIGS. 2 and 3. At this time a set gas pressure within chamber 20 is achieved and at this pressure the annular wall 40 presses against the stomach mucosa 70 as shown, with a contact force thereby sealing the antral pouch 7. As food is ingested into the stomach 5 it presses down on the superior wall 30, as shown in FIG. 4, causing this wall to assume a concave shape. Since inferior wall 50 is relatively rigid, the gas pressure within chamber 20 rises as the total volume of the anteral chamber 20 drops, and this causes a greater sealing force to be applied by annular wall 40 against the stomach's interior wall surface (mucosa) 6. It should be noticed also that food entering the antral pouch 7 tends to move against the intersection of the superior wall 30 and the mucosa 6 so that a flushing liquid does not easily come into contact with the annular wall's outside surface which is pressing against the mucosa 6. This is due to the concave shape that superior wall 30 assumes when the weight of food 100 presses down on it, which causes food to move radially away from valve 80, that is toward mucosa 6. This effect also helps to prevent the flushing of food out of the antral pouch 7 and avoids this problem as previously described above.

What is claimed is:

1. A bariatric balloon for placement within a human stomach, the human stomach having an antral pouch position for receiving food into the stomach, a pyloric sphincter for discharging digested food from the stomach, and a mucosa lining of the stomach, the bariatric balloon comprising:
    an antral chamber having a gas pressure therein, the antral chamber having a shape and size for contact with the mucosa lining of the stomach adjacent the antral pouch;
    the antral chamber having:
        an elastic superior wall having a convex shape forced by the gas pressure within the antral chamber, the superior wall facing the antral pouch of the stomach;
        a non-elastic inferior wall having a planar shape, said superior and inferior walls mutually spaced apart for defining a volume of the antral chamber; and
        an annular wall having a cylindrical shape, the annular wall: (i) joined at an upper periphery thereof with the elastic superior wall, (ii) joined at a lower periphery thereof with the non-elastic inferior wall, (iii) having an elasticity between that of the elastic superior wall and the non-elastic inferior wall; and (iv) positioned against and pressed against the mucosa lining by the gas pressure within the antral chamber;
    a gas filled pyloric chamber joined with, and positioned below, the antral chamber, a pyloric chamber wall encompassing the pyloric chamber and positioned in contact with the mucosa lining; and
    together, the gas-filled antral and pyloric chambers defining a volume less than a volume of the human stomach.

2. The bariatric balloon of claim 1 further comprising a tubular valve positioned within the antral and pyloric chambers, the tubular valve having a means for exchanging gas with the chambers, and still further comprising at least two safety arms, secured to, and extending radially outwardly from the tubular valve, the arms having a length and circumference greater than an opening of the pyloric sphincter, whereby, upon deflation of the bariatric balloon within the stomach, the safety arms prevent the bariatric balloon from passing through the pyloric sphincter.

3. The bariatric balloon of claim 1 wherein at least one of the annular wall, and the pyloric chamber wall has an external open channel thereon, the open channel enabled by size and extent for passing digested food from the antral pouch toward the pyloric sphincter.

4. The bariatric balloon of claim 1 further comprising at least two safety arms secured to and extending radially outwardly from the bariatric balloon, the arms having a length and circumference greater then an opening of the pyloric sphincter of the stomach, whereby, upon deflation of the bariatric balloon within the stomach, the safety arms prevent the bariatric balloon from passing through the pyloric sphincter.

5. The bariatric balloon of claim 1 wherein the superior wall has an elasticity enabling inversion of the superior wall from said convex shape to a concave shape when the superior wall receives sufficient food thereon, wherein, the antral chamber gas pressure and the pressure of the annular wall against the mucosa lining is thereby increased, whereby, passage of undigested food between the annular wall and the mucosa lining is inhibited.

* * * * *